US00PP13785P29

(12) United States Plant Patent
Oudolf

(10) Patent No.: US PP13,785 P2
(45) Date of Patent: May 6, 2003

(54) GERANIUM PLANT NAMED 'SPRINGTIME'

(75) Inventor: Petrus Hendricus Oudolf, De Hummelo (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 10/139,959

(22) Filed: May 6, 2002

(51) Int. Cl.[7] ..... A01H 5/00
(52) U.S. Cl. ..... Plt./324
(58) Field of Search ..... Plt./324

*Primary Examiner*—Kent Bell
(74) *Attorney, Agent, or Firm*—C. A. Whealy

(57) ABSTRACT

A distinct cultivar of Geranium plant named 'Springtime', characterized by its upright plant habit; variegated leaves; and dark purple-colored flowers.

1 Drawing Sheet

BOTANICAL CLASSIFICATION/CULTIVAR DESIGNATION

*Geranium phaeum* cultivar 'Springtime'.

BACKGROUND OF THE INVENTION

The present Invention relates to a new and distinct cultivar of Geranium plant, botanically known as *Geranium phaeum*, and hereinafter referred to by the cultivar name Springtime.

The new Geranium originated from a chance cross-pollination of two unidentified selections of *Geranium phaeum*, not patented. The new Geranium was discovered by the Inventor in 1999 in Hummelo, The Netherlands. Plants of the new Geranium differed primarily from plants of the unidentified parental selections in leaf and flower coloration.

Asexual reproduction of the new cultivar by cuttings in Hummelo, The Netherlands since 1999, has shown that the unique features of this new Geranium are stable and reproduced true to type in successive generations.

SUMMARY OF THE INVENTION

Plants of the cultivar Springtime have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Springtime'. These characteristics in combination distinguish 'Springtime' as a new and distinct cultivar:

1. Upright plant habit.
2. Variegated leaves.
3. Dark purple-colored flowers.

Plants of the new Geranium can be compared to plants of the Geranium cultivar Samobor, not patented. In side-by-side comparisons conducted in Hummelo, The Netherlands, plants of the new Geranium differed from of the cultivar Samobor in the following characteristics:

1. Plants of the new Geranium had variegated foliage whereas plants of the cultivar Samobor had solid green foliage.
2. Plants of the new Geranium had darker purple-colored flowers than plants of the cultivar Samobor.

BRIEF DESCRIPTION OF THE PHOTOGRAPHS

The accompanying colored photographs illustrate the overall appearance of the new Geranium, showing the colors as true as it is reasonably possible to obtain in colored reproductions of this type. Colors in the photographs may differ slightly from the color values cited in the detailed botanical description which accurately describe the colors of the new Geranium.

The photograph at the top of the sheet comprises a side perspective view of typical one-year old flowering plants of 'Springtime' grown in containers.

The photograph at the bottom of the sheet comprises a close up view of typical flowers of 'Springtime'.

DETAILED BOTANICAL DESCRIPTION

In the following description, color references are made to The Royal Horticultural Society Colour Chart, 2001 Edition, except where general terms of ordinary dictionary significance are used. Plants used for the following description were about one year old and grown under outdoor field conditions which closely approximate commercial production conditions during the spring and summer in Hummelo, The Netherlands.

Botanical classification: *Geranium phaeum* cultivar Springtime.

Parentage: Cross-pollination of two unidentified selections of *Geranium phaeum*, not patented.

Propagation:

*Type.*—By cuttings.

*Time to produce a rooted young plant.*—About 30 days at 18 to 20° C.

*Root description.*—Thick, somewhat fleshy, brown in color.

Plant description:

*Form.*—Perennial flowering plant; upright plant habit; freely basal branching; vigorous growth habit.

*Plant height.*—About 45 cm.

*Plant diameter.*—About 35 cm.

*Basal branch description.*—Number per plant: About four to six. Length: About 45 cm. Diameter: About 2 mm. Internode length: About 6 cm. Strength: Moderately strong. Texture: Pubescent. Color: Mostly 144A to 144B; occasionally tinged with 182B.

*Foliage description.*—Arrangement: Alternate, simple. Length: About 3.5 cm. Width: About 6 cm. Shape: Palmately lobed. Apex: Acute. Base: Hastate. Margin: Serrate to incised. Texture, upper and lower surfaces: Pubescent. Venation pattern: Palmate. Petiole: Length: About 3 cm. Diameter: About 1.5 mm. Texture: Pubescent. Color: Young foliage, upper surface: Center, 149D; towards margins, 137C to 137D; random dark red, 183A to 183B, midway between base and margins. Young foliage, lower surface: Center, 145B to 145C; towards margins, 138B. Fully expanded foliage, upper surface: Center, 149C to 149D; towards margins, 137A; random dark red, 183A to 183B, midway between base and margins. Fully expanded foliage, lower surface: Center, 145B to 145C; towards margins, 137A to 137B. Venation, upper surface: 149C to 149D. Venation, lower surface: 145B to 145C; towards the margins, 137A to 137B. Petiole: 145B to 145C.

*Stipule description.*—Quantity: Two stipules per internode. Length: About 1 cm. Width: About 5 mm. Shape: Lanceolate. Texture, upper and lower surfaces: Pubescent. Color: 164A to 165B.

Flower description:

*Appearance.*—Single rotate flowers with five petals arranged in terminal and axillary umbels; usually two flowers per umbel. Flowers not persistent.

*Quantity of flowers.*—About 100 flowers per plant develop during the flowering season.

*Natural flowering season.*—May through June in Hummelo, The Netherlands.

*Fragrance.*—None detected.

*Flower longevity.*—About one to two weeks.

*Inflorescence height.*—About 25 cm.

*Inflorescence diameter.*—About 10 cm.

*Flower diameter.*—About 2.4 cm.

*Flower depth* (*height*).—About 1 cm.

*Flower buds.*—Length: About 6 mm. Diameter: About 1.8 cm. Shape: Ovoid. Color: 143A.

*Petals.*—Quantity per flower: Five. Arrangement: Rotate, slightly overlapping. Length: About 1.3 cm. Width: About 1.2 cm. Shape: Rhomboid to flabellate. Apex: Rounded to retuse. Base: Cuspidate. Margin: Entire. Texture, upper and lower surfaces: Smooth, glabrous. Color: When opening, upper and lower surfaces: Slightly more red than 187A. Fully opened, upper and lower surfaces: Slightly more red than 187B.

*Sepals.*—Quantity per flower: Five. Arrangement: Rotate. Calyx length: About 3 mm. Calyx width: About 1.8 cm. Sepal shape: Narrowly lanceolate. Sepal apex: Mucronate. Sepal margin: Entire. Sepal texture, upper surface: Smooth, glabrous. Sepal texture, lower surface: Pubescent. Color, upper and lower surfaces: 146A overlain with 181A.

*Peduncles.*—Length: About 3.5 cm. Diameter: About 1 mm. Angle: About 30 to 50° from vertical. Strength: Strong. Color: 144A to 144B.

*Pedicels.*—Length: About 1.8 cm. Diameter: Less than 1 mm. Angle: About 10 to 20° from vertical. Strength: Strong. Color: 144A to 144B; towards the flowers, overlain with 181A.

*Reproductive organs.*—Stamens: Quantity per flower: Ten. Anther shape: Oblong; dorsifixed. Anther length: About 2 mm. Anther diameter: About 0.5 mm. Anther color: Close to 156D. Pollen amount: Scarce. Pollen color: 7A. Pistils: Quantity per flower: Five; fused. Pistil length: About 6 mm. Style length: About 5 mm. Style color: 143B. Stigma color: 143B overlain with 181C. Ovary color: 143B to 143C.

*Fruit.*—Quantity per plant: About 100. Length: About 1.5 cm. Diameter: About 5 mm. Color: Close to 187A.

*Seed.*—Quantity per fruit: About 26. Length: About 1 mm. Diameter: About 1 mm. Color: Close to 200B.

Disease/pest resistance: Plants of the new Geranium have not been noted to be resistant to pathogens or pests common to Geranium.

Temperature tolerance: Plants of the new Geranium are tolerant to temperatures from about −20 to 35° C.

It is claimed:

1. A new and distinct cultivar of Geranium plant named 'Springtime', as illustrated and described.

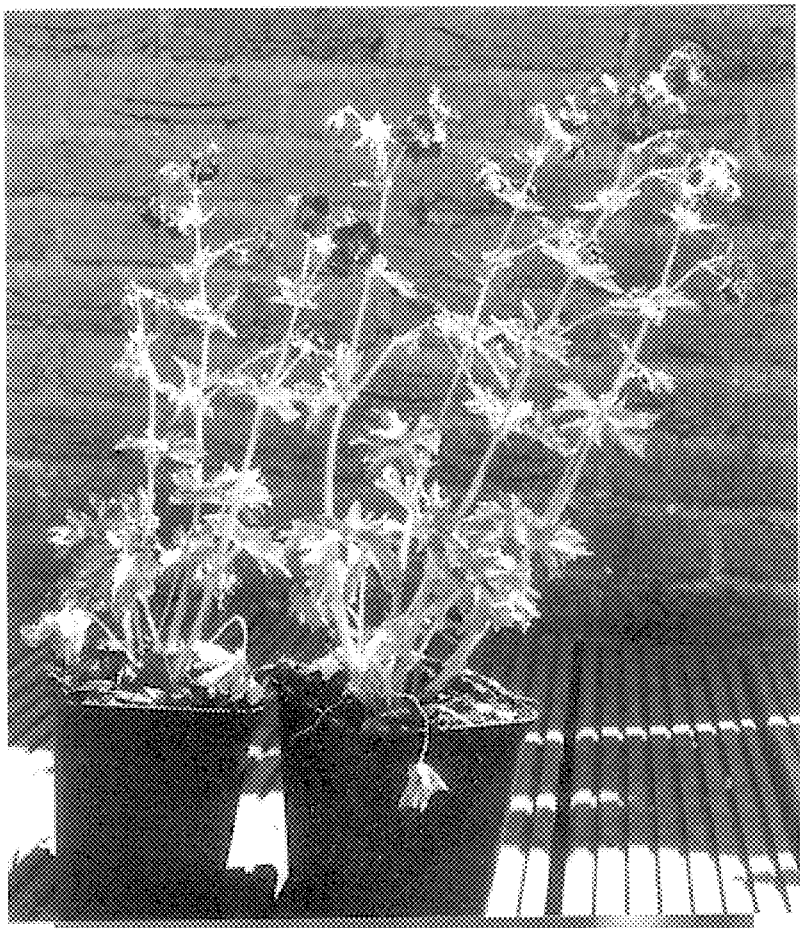
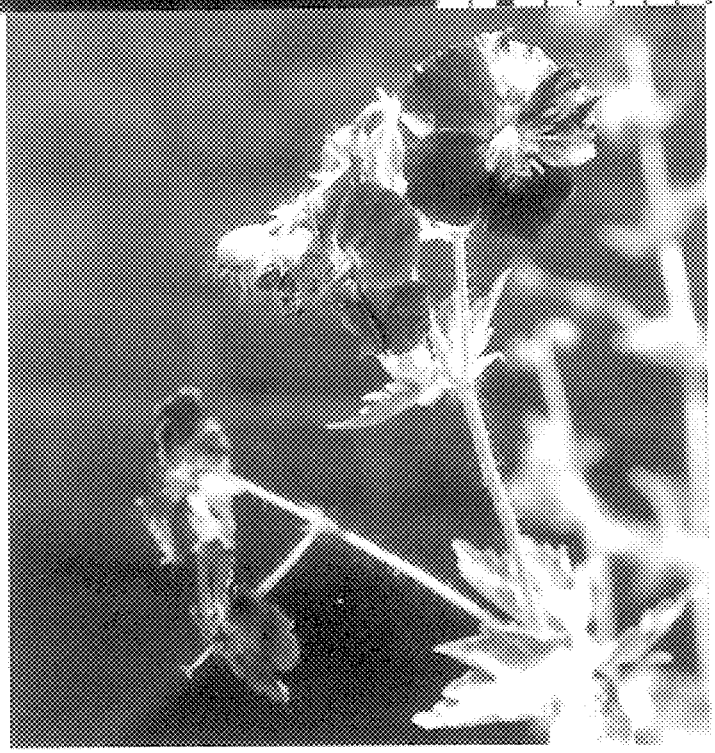

* * * * *